United States Patent
Berberich

(10) Patent No.: US 8,796,592 B2
(45) Date of Patent: Aug. 5, 2014

(54) STAINING DEVICE HAVING AUTOMATIC MAINS VOLTAGE DETECTION AND VOLTAGE CHANGEOVER

(75) Inventor: Markus Berberich, Heldelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 571 days.

(21) Appl. No.: 13/176,635

(22) Filed: Jul. 5, 2011

(65) Prior Publication Data

US 2012/0006807 A1 Jan. 12, 2012

(30) Foreign Application Priority Data

Jul. 9, 2010 (DE) .......................... 10 2010 036 318

(51) Int. Cl.
*H05B 1/02* (2006.01)
*G01N 1/31* (2006.01)

(52) U.S. Cl.
CPC ...................................... *G01N 1/312* (2013.01)
USPC ............ 219/486; 219/509; 219/497; 219/483

(58) Field of Classification Search
CPC .. H05B 1/0202; H05B 1/0288; H05B 3/0014; H05B 3/026; G01N 1/312
USPC .......................... 219/483, 486, 507–509, 497
See application file for complete search history.

(56) References Cited

U.S. PATENT DOCUMENTS

| | | | | |
|---|---|---|---|---|
| 4,215,268 A | * | 7/1980 | Dinkel | 219/507 |
| 4,340,850 A | * | 7/1982 | Segars | 323/218 |
| 5,601,650 A | | 2/1997 | Goldbecker et al. | |
| 2006/0263073 A1 | * | 11/2006 | Clarke et al. | 392/347 |
| 2009/0304370 A1 | * | 12/2009 | Dupuis | 392/407 |
| 2010/0213185 A1 | | 8/2010 | Miller | |

FOREIGN PATENT DOCUMENTS

| | | |
|---|---|---|
| DE | 719108 | 3/1942 |
| DE | 825441 | 12/1951 |
| DE | 1059550 | 6/1959 |
| DE | 4117833 | 12/1992 |
| WO | 2008101583 | 8/2008 |

\* cited by examiner

*Primary Examiner* — Mark Paschall
(74) *Attorney, Agent, or Firm* — Schlee IP International, P.C.; Alexander R. Schlee

(57) ABSTRACT

A staining device for staining samples has a heating device including a first heating element and a second heating element. A switch arrangement allows the two heating elements to be connected in parallel or in series. A power connection supplies power to the heating elements. A sensor is designed and located to detect a current supplied to the heating elements. A switching unit is coupled to the sensor and determines a voltage causing the current. Depending on the voltage, the switching unit connects the heating elements in parallel or in series.

5 Claims, 3 Drawing Sheets

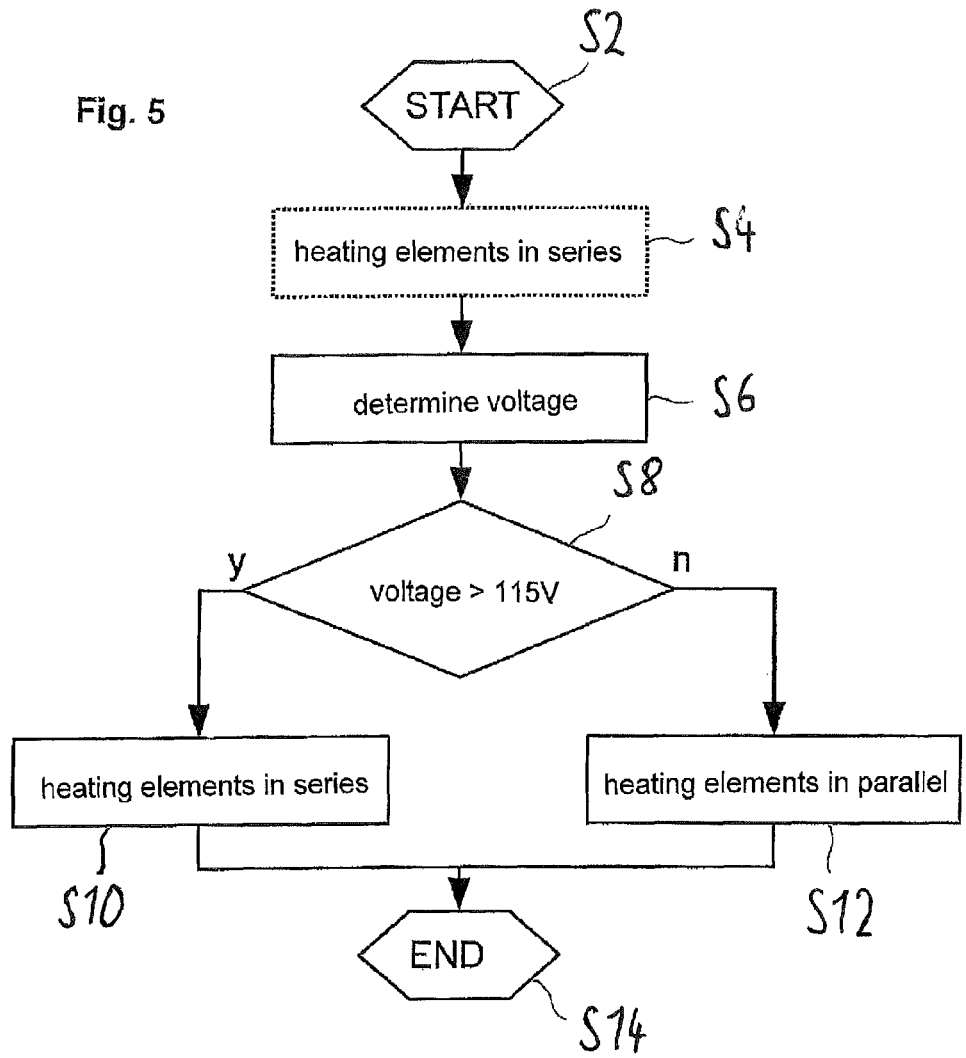

STAINING DEVICE HAVING AUTOMATIC MAINS VOLTAGE DETECTION AND VOLTAGE CHANGEOVER

CROSS-REFERENCE TO RELATED APPLICATION

This application claims the priority of the German patent application DE 102010036318.9 having a filing date of Jul. 9, 2010. The entire content of this prior German patent application DE 102010036318.9 is herewith incorporated by reference.

BACKGROUND OF THE INVENTION

The present invention relates to a staining device for staining samples. The staining device has a heating device including a first and a second heating element. Further provided is a power connection for supplying power to the heating elements. The present invention also relates to a method for operating the staining device.

Samples, in particular tissue samples to be examined using a microscope, are routinely stained using staining devices, so that structures of the samples can be better seen in the microscopic image than in the case of unstained samples. For sample staining, a staining device includes two or more containers in which identical, similar or different process media are stored. The samples to be stained are immersed in the process media, where they remain for residence times which are dependent on the process step, the process medium, and on the sample to be stained. Once the predetermined residence time has elapsed, the samples are withdrawn from the container and transferred to the next container by means of a transport system. Depending on the staining method and/or the sample, the samples are in this manner successively immersed in a plurality of containers filled with process media. Moreover, the samples may be dried before, between or after the aforementioned steps, using an oven. For example, moist sections of paraffin-embedded tissue samples placed on slides may be dried in the oven, thereby evaporating the moisture and partially melting the paraffin, which improves the adherence of the tissue samples to the slides.

The staining device has a heating device, which is part of the oven or is provided for heating the process media in the containers. The heating device may have one or more heating elements. The staining device and, in particular, the heating elements, may be operated at different voltages, for example at 115 volts and at 220 volts. Depending on the available mains voltage, the staining device can be manually switched to operate at 220 volts or to operate at 115 volts.

From the document DE 41 17 833 A1, a device for staining histological samples arranged on slides is known, which comprises heatable liquid containers.

Document DE 1 059 550 B describes an electrical heating system that can be operated with different voltages so that the electrical heating can be used in the international train traffic at different operating voltages.

From the document WO 2008/101583 A1, a furnace for dental prostheses and partial dental prostheses is known, in which for preventing damage to the heating elements switching between a series connection and a parallel connection of the heating elements is possible.

Document DE 719 108 A describes a transformer-free universal receiver for the optional connection to DC networks or AC networks with different supply voltages.

From the document DE 825 441 B, a baby bottle warmer is known which comprises a heating jacket surrounding the bottle.

It is an object of the present invention to provide a staining device and a method for operating the staining device, which, in a simple manner, will enable the staining device to be safely and effectively operated at different voltages.

SUMMARY OF THE INVENTION

This object is achieved according to a first aspect of the invention by a staining device for staining samples, comprising: a heating device including a first heating element and a second heating element; a switch arrangement designed to switch between a first operating mode connecting the two heating elements in series and a second operating mode connecting the two heating elements in parallel; a power connection supplying power to the heating elements; a sensor designed and located to detect an amperage of a current supplied to the heating elements; and a switching unit that is coupled to the sensor and determines based on the amperage a voltage causing the current, and switches depending on the determined voltage via the switch arrangement into the first operating mode or the second operating mode.

This object is achieved according to a second aspect of the invention by a method for operating a staining device for staining samples, the staining device comprising a first heating element and a second heating element, both heating elements being supplied with electric current, wherein the first and second heating elements are electrically connectable in a first operating mode in series and in a second operating mode in parallel, said method comprising the following subsequent method steps: a) connecting the first and second heating elements initially by default according the first operating mode in series; b) subsequently detecting an amperage of the current supplied to the heating elements and determining based on the amperage a voltage causing the current; and c) switching from the first operating mode into the second operating mode if the voltage is below a certain threshold voltage.

A switch arrangement allows the two heating elements to be connected in parallel or in series. A sensor is designed and located to detect a current supplied to the heating elements. Based on the current, a switching unit coupled to the sensor determines a voltage which causes the current. Depending on the voltage, the switching unit connects the heating elements in parallel or in series.

DETAILED DESCRIPTION OF THE INVENTION

In this manner, the heating elements can be switched automatically according to the available mains voltage. This prevents the heating elements both from being overloaded by excessive voltage and from being operated at too low a power level, which would result in ineffective heating. Thus, the automatic detection of the voltage and the corresponding switching of the heating elements contribute to safe and effective operation of the staining device. Current detection means, for example, to measure a current intensity, a current flow, a magnetic field generated by the current flow, or a different physical quantity, on the basis of which the current can be determined. In particular, it is preferred to measure the current that is fed to the heating elements via a power connection of the staining device. The power connection includes, for example, a current conductor or a power plug.

In one embodiment, the switching unit connects the heating elements in series at a first voltage and in parallel at a second voltage that is lower than the first voltage. The first voltage is, for example, 220 volts and the second voltage is, for example, 115 volts. At the higher voltage, the heating elements are connected in series, so that the high voltage is divided into two lower voltages applied to the heating elements, thereby preventing overloading of one or both of the heating elements by the high voltage. When the heating elements are operated at the lower, second voltage, then the heating elements are connected in parallel, so that the same voltage, in particular the available mains voltage, is applied to each of the heating elements. This helps operate the heating elements in the most effective manner possible.

In another embodiment, the sensor includes a Hall-effect element disposed near the power connection. In this context, the power connection includes all components of the staining device that carry the electric current to the heating elements when the mains voltage is available. These components include, for example, plugs, connectors and/or electrical leads of the staining device. By default, the heating elements are preferably connected in series, so that by default the available voltage is divided among the two heating elements, thereby preventing overloading of the heating elements.

In a second aspect of the present invention, the current supplied to the staining device is determined, and the heating elements of the staining device are connected in series or in parallel, depending on the voltage that causes the current. Preferably, the heating elements are connected in series at a first voltage and in parallel at a second voltage that is lower than the first voltage. The voltage may be determined as a function of the determined current.

BRIEF DESCRIPTION OF THE DRAWINGS

Exemplary embodiments of the present invention are described in more detail below with reference to the schematic drawings, in which:

FIG. 5 is a flow chart of a program for operating the staining device.

DETAILED DESCRIPTION OF THE DRAWINGS

Figure 1:
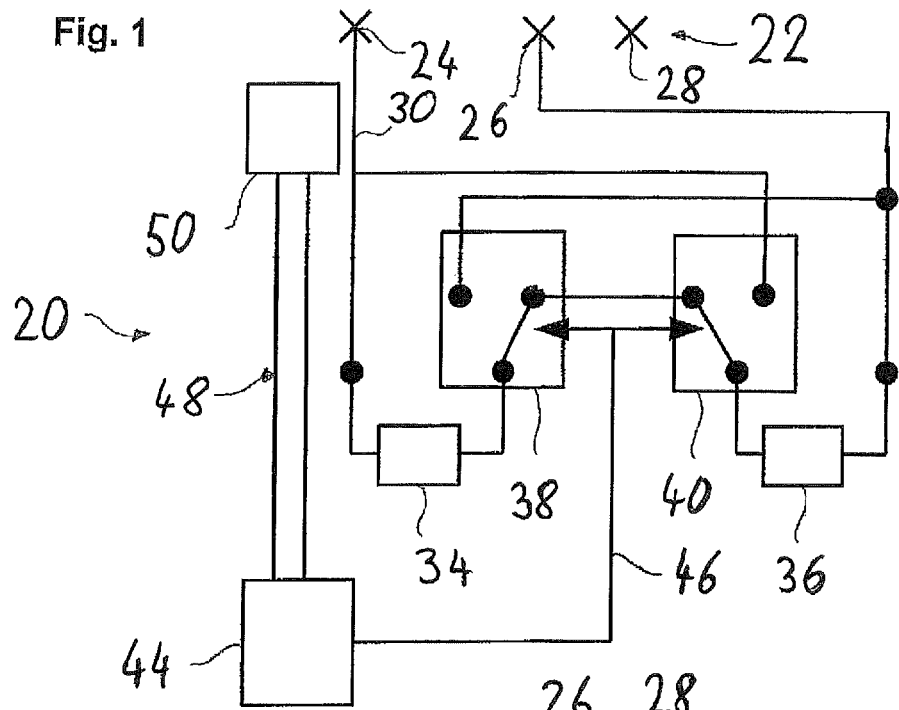
FIG. 1 is a view of a first embodiment of a heating device of a staining device, shown in a first connection state.

Elements having the same design or function are identified by the same reference numerals throughout the figures.

FIG. 1 shows a heating device 20 of a staining device. The staining device is suitable for staining samples, such as tissue samples, for subsequent examination under a microscope. The staining device includes a plurality of containers (not shown) filled with process media, said process media being used to wash, dehydrate and/or stain the samples. Heating device 20 is used to heat the process media stored in the containers or keep them at a predetermined temperature, or to dry the samples.

The heating device is connected to a power supply 22. Power supply 22 includes a forward conductor 24, a return conductor 26, and a grounding conductor 28. Forward conductor 24 may be the current-carrying conductor, and return conductor 26 may be the neutral conductor. Alternatively, forward conductor 24 may be the neutral conductor, and return conductor 26 may be the current-carrying conductor. A power connection of the staining device, in particular of heating device 20, is connected to power supply 22. The power connection of heating device 20 specifically includes a current conductor 30 via which the voltage and current provided by the mains power supply are delivered to the modules of heating device 20. In addition, the power connection may further include additional current conductors 30, connectors, plugs and/or transformers of heating device 20.

Current conductor 30 is connected firstly to a first heating element 34. Return conductor 26 is coupled to a second heating element 36. Further, first heating element 34 is connected to a first switch 38, and second heating element 36 is connected to a second switch 40. Moreover, first switch 38 is connected to return conductor 26, and second switch 40 is connected to current conductor 30. A switching unit 44 operates first and second switches 38, 40 via a control line 46. Switching unit 44 is connected to a sensing element, in particular a Hall-effect sensor 50, via a sensor line 48. Hall-effect sensor 50 is located so close to the power connection, in particular to current conductor 30, that is it able to measure a magnetic field generated around current conductor 30 by the current flowing therein during operation. The current flowing through current conductor 30, in particular the current intensity, current flow or current density, can be determined as a function of the magnetic field, and the voltage present at the power connection can be determined as a function of the current.

In a first connection state of switches 38, 40, the two switches 38, 40 are coupled to each other directly, so that the two heating elements 34, 36 are connected in series. A mains voltage provided via power supply 22 is then divided among the two heating elements 34, 36 according to the resistances thereof, so that if the resistances are the same, then the same voltage is applied to each of heating elements 34, 36, and the available voltage is divided. The first connection state is preferably activated at a high first voltage of, for example, at 220 volts. In addition, the first connection state is preferably selected by default; i.e., when the staining device is turned on, so that overloading of heating elements 34, 36 is reliably prevented.

Figure 2:
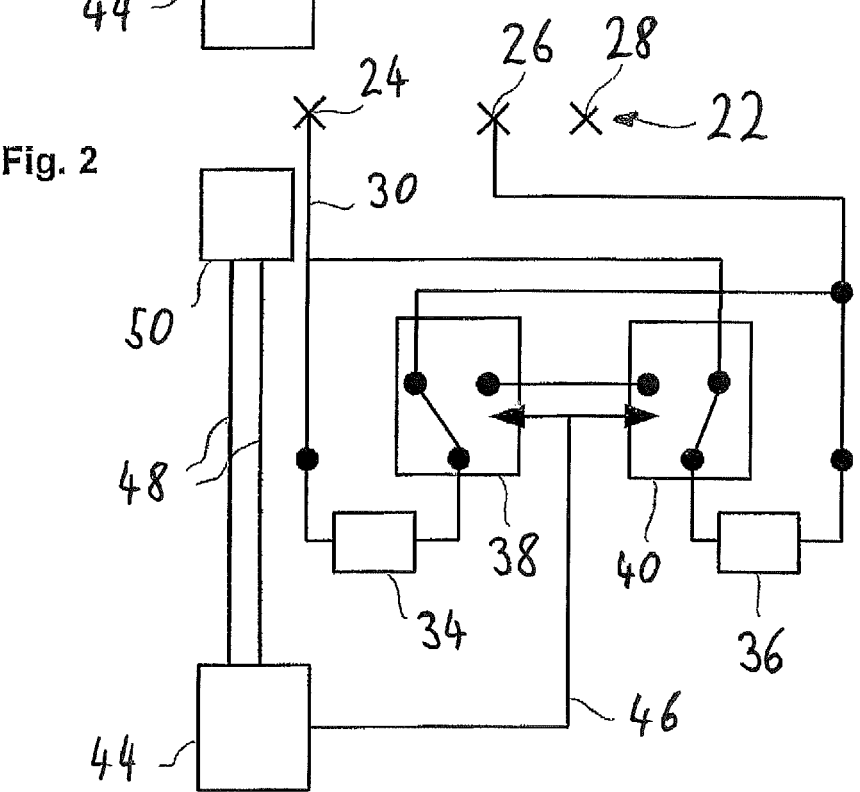
FIG. 2 is a view of the heating device of FIG. 1, shown in a second connection state.

FIG. 2 shows the heating device 20 of FIG. 1 in a second connection state. In the second connection state, switch 38 is connected to first heating element 34 and to return conductor 26. Second switch 40 is connected to second heating element 36 and to current conductor 30. As a result of this, the two heating elements 34, 36 are connected in parallel. Thus, if heating elements 34, 36 are of the same type, then the same voltage is applied to both heating elements 34, 36, so that the two heating elements 34, 36 are operated at the full voltage provided by power supply 22. The second connection state is preferably activated at a second, relatively low voltage, in particular at 115 volts. As a result, despite the low mains voltage available, heating elements 34, 36 are still operated at the maximum available voltage, which is particularly effective.

Figure 3:
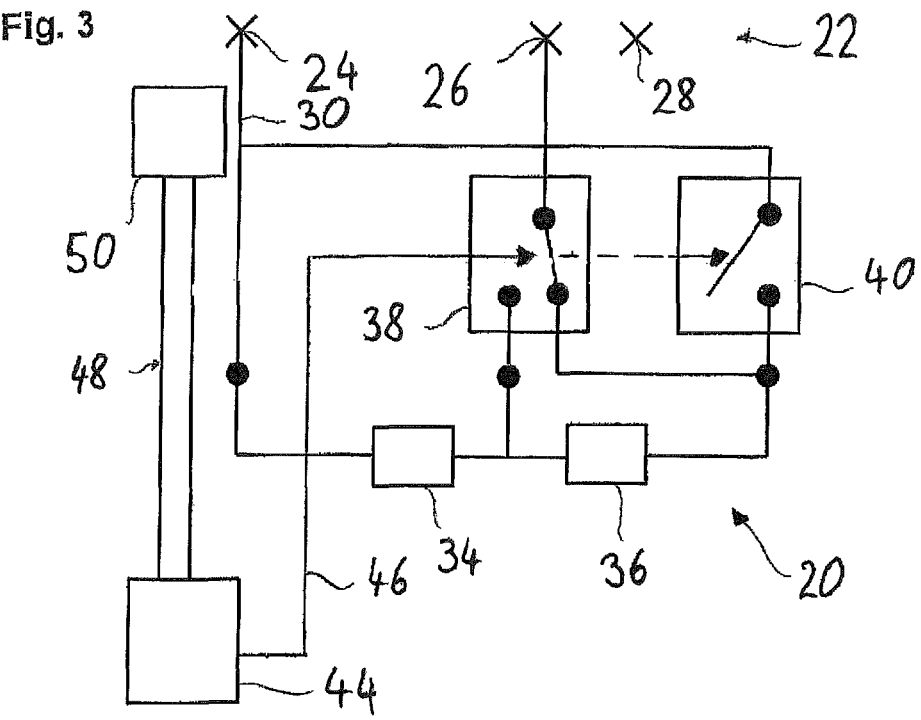
FIG. 3 is a view of a second embodiment of the heating device, shown in a first connection state.

FIG. 3 shows a second embodiment of heating device 20. The second embodiment of heating device 20 is also connected to power supply 22, which includes current-carrying conductor 24, return conductor 26 and grounding conductor 28. Current conductor 30 of the power connection of heating device 20 is connected to first heating element 34 and to second switch 40. First heating element 34 is connected to first switch 38 and to second heating element 36. Second heating element 36 is connected to first heating element 34, to first switch 38, and to second switch 40.

In the first connection state shown, first switch 38 couples second heating element 36 to return conductor 26 in such a manner that first and second heating elements 34, 36 are connected in series. Hall-effect sensor 50 measures the voltage in current conductor 30, and the two switches 38, 40 are operated as a function of the measured voltage.

Figure 4:
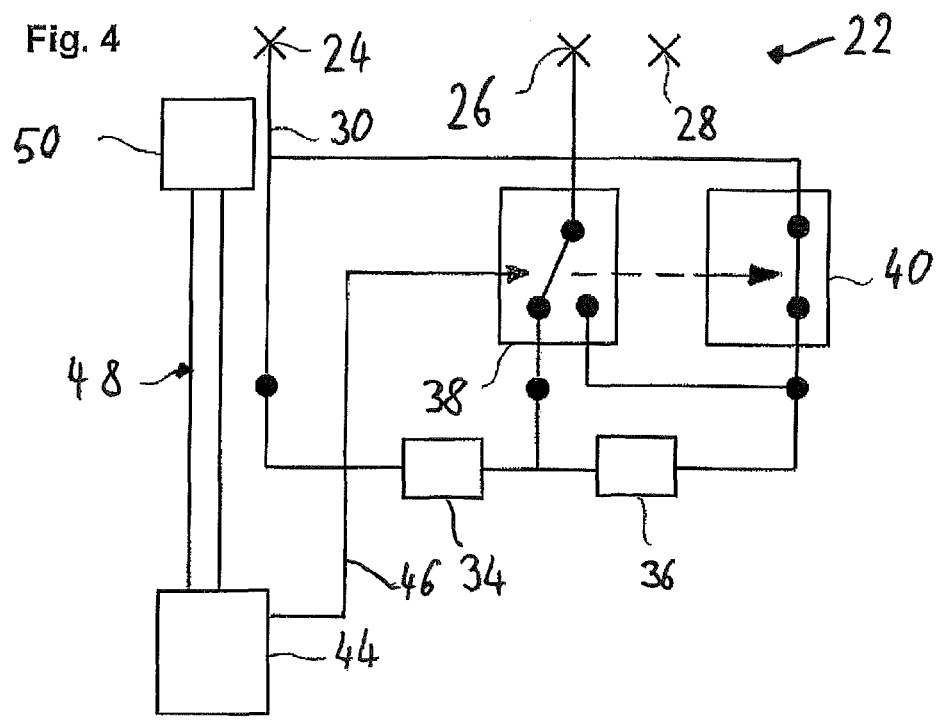
FIG. 4 is a view of the second embodiment of the heating device, shown in a second connection state.

FIG. 4 shows the embodiment of heating device 20 of FIG. 3 in a second connection state. In the second connection state, first switch 38 couples first heating element 34 to return conductor 26 and decouples second heating element 36 from return conductor 26. Second switch 40 couples second heating element 36 to current conductor 30, so that first and second heating elements 34, 36 are connected in parallel.

In order to detect the mains voltage automatically, and to switch heating device 20, and specifically the two switches 38, 40, accordingly, a program for operating the staining device is stored on a storage device of the staining device. The program is used to prevent heating elements 34, 36 from being overloaded by excessive voltage applied thereto, and from receiving too little current when a low voltage is applied.

The program is preferably started in a step S2, in which variables are initialized if necessary, for example shortly after the staining device is started.

In a step S4, heating elements 34, 36 may be connected in series by default. In this manner, heating elements 34, 36 are prevented from being overloaded when the first, high voltage is present at power-up, and thus, the staining device is prevented from being damaged.

In a step S6, the voltage present at the power connection is determined. The voltage may be determined directly or indirectly. In order to determine the voltage indirectly, preferably, the magnetic field generated by the current through current conductor 30 is determined, after which the current is determined as a function of the magnetic field, and the voltage is determined as a function of the current. Alternatively, the current may be measured directly, and the voltage may then be determined as a function of the current. Direct measurement of the voltage may be accomplished using, for example, a voltmeter.

In a step S8, it is checked whether the voltage is greater than a second voltage, in particular 115 volts. If the condition of step S8 is satisfied, then the processing is continued in a step S10. If the condition of step S8 is not satisfied, then the processing is continued in a step S12.

In step S10, heating elements 34, 36 are connected in series by switching heating device 20 to the first connection state.

In step S12, heating elements 34, 36 are connected in parallel by switching heating device 20 to the first connection state.

In a step S14, the program may be terminated. Preferably, the program is executed each time the staining device is disconnected from power supply 22 and reconnected to power supply 22 or connected to a different power supply.

The present invention is not limited to the exemplary embodiments described herein. For example, a different sensor, such as a conventional voltmeter, may be used in place of Hall-effect sensor 50 for detecting the applied voltage. Moreover, it is possible to provide more than the two heating elements 34, 36, which are then alternatively connected in parallel or series, or which replace one of the two heating elements 34, 36 and are connected in series.

LIST OF REFERENCE NUMERALS 20 heating device
22 power supply
24 forward conductor
26 return conductor
28 grounding conductor
30 current conductor
34 first heating element
36 second heating element
38 first switch
40 second switch
44 switching unit
46 control line
48 sensor line
50 Hall-effect sensor
S2-S14 steps two through fourteen

What is claimed is:

1. A staining device for staining samples, comprising:
a heating device including a first heating element and a second heating element;
a switch arrangement designed to switch between a first operating mode connecting the two heating elements in series and a second operating mode connecting the two heating elements in parallel;
a power connection supplying power to the heating elements;
a sensor designed and located to detect an amperage of a current supplied to the heating elements; and
a switching unit that is coupled to the sensor and determines based on the amperage a voltage causing the current, and switches depending on the determined voltage via the switch arrangement into the first operating mode or the second operating mode; wherein
the switching unit is configured to connect the heating elements in series at 220 V and in parallel at 115 V so that the 220 V voltage is divided into two lower voltages applied to the heating elements, thereby preventing overloading of one or both of the heating elements by the 220 V high voltage and securing the available mains voltage when the heating elements are operated at the 115 V voltage and therefore switched in parallel.

2. The staining device as recited in claim 1,
wherein the sensor includes a Hall-effect element positioned close to the power connection.

3. The staining device as recited in claim 1,
wherein the heating elements are by default connected in series.

4. A method for operating a staining device for staining samples, the staining device comprising a first heating element and a second heating element, both heating elements being supplied with electric current, wherein the first and second heating elements are electrically connectable in a first operating mode at 220 V in series and in a second operating mode at 115 V in parallel, said method comprising the following subsequent method steps:
a) connecting the first and second heating elements initially by default according the first operating mode at 220 V in series;
b) subsequently detecting an amperage of the current supplied to the heating elements and determining a voltage based on the detected amperage; and
c) switching from the first operating mode into the second operating mode where the heating elements are connected in parallel if the voltage is at or below 115 V.

5. The method as recited in claim 4, comprising detecting a magnetic field strength generated by a power connection of the staining device and deriving the amperage from the detected magnetic field strength.

* * * * *

UNITED STATES PATENT AND TRADEMARK OFFICE
CERTIFICATE OF CORRECTION

| | | |
|---|---|---|
| PATENT NO. | : 8,796,592 B2 | Page 1 of 1 |
| APPLICATION NO. | : 13/176635 | |
| DATED | : August 5, 2014 | |
| INVENTOR(S) | : Markus Berberich | |

It is certified that error appears in the above-identified patent and that said Letters Patent is hereby corrected as shown below:

On the Title page of the patent, Item (75) the inventor's information reads:

Markus Berberich, Heldelberg (DE)

and should read:

Markus Berberich, Heidelberg (DE)

Signed and Sealed this
Twenty-first Day of October, 2014

Michelle K. Lee
*Deputy Director of the United States Patent and Trademark Office*